(12) United States Patent
Kobayashi et al.

(10) Patent No.: US 7,543,732 B2
(45) Date of Patent: Jun. 9, 2009

(54) EVALUATION METHOD AND EVALUATION APPARATUS FOR SPOT WELDED PORTION

(75) Inventors: Eiichi Kobayashi, Aichi (JP); Yusuke Kondo, Aichi (JP); Hisayuki Ishizu, Aichi (JP); Nobutaka Oda, Gifu (JP); Kazuo Ao, Aichi (JP)

(73) Assignee: Mitsubishi Jidosha Kogyo Kabushiki Kaisha, Tokyo (JP)

( * ) Notice: Subject to any disclaimer, the term of this patent is extended or adjusted under 35 U.S.C. 154(b) by 201 days.

(21) Appl. No.: 10/849,140

(22) Filed: May 20, 2004

(65) Prior Publication Data

US 2004/0262365 A1 Dec. 30, 2004

(30) Foreign Application Priority Data

May 23, 2003 (JP) ............................. 2003-146373
May 23, 2003 (JP) ............................. 2003-146374

(51) Int. Cl.
*B23K 31/12* (2006.01)
(52) U.S. Cl. ................... 228/103; 219/110; 148/500
(58) Field of Classification Search ............. 228/103; 148/500, 503; 700/145; 219/110, 109, 130.01
See application file for complete search history.

(56) References Cited

U.S. PATENT DOCUMENTS

| 5,883,312 | A | 3/1999 | Hayashida |  |
|---|---|---|---|---|
| 5,930,155 | A | 7/1999 | Tohi et al. |  |
| 6,398,102 | B1 * | 6/2002 | Cao et al. | 228/103 |
| 6,535,211 | B1 * | 3/2003 | Hariya et al. | 345/423 |
| 6,901,809 | B2 * | 6/2005 | Dong et al. | 73/789 |

(Continued)

FOREIGN PATENT DOCUMENTS

DE 197 58 122 7/1999

(Continued)

OTHER PUBLICATIONS

Yuji et al. "Method of Fatigue Life estimation for Spot-Welding Structures", Society of Automobile engineers, Inc. 2000.*

(Continued)

*Primary Examiner*—Jessica L Ward
*Assistant Examiner*—Michael Aboagye
(74) *Attorney, Agent, or Firm*—Birch, Stewart, Kolasch & Birch, LLP (57) ABSTRACT

A technique for evaluation of the strength of a spot welded portion of a panel is provided. A stress value at the welded portion of the panel is calculated by a stress analysis according to a FEM using the elements, and then the strength of the welded portion is evaluated based on the stress value at the welded portion. A portion in the proximity of the spot welded portion is divided, with a central portion of the spot welded portion registered with a nodal point of the elements, into a central element and plural concentric ring-like elements from the center side provided by the central portion of the spot welded portion. Thereafter, the plural concentric ring-like elements are individually divided in a circumferential direction each into a plurality of portions to form the elements. Then, the strength is evaluated based on the stress value of the second ring-like element.

8 Claims, 9 Drawing Sheets

U.S. PATENT DOCUMENTS

2002/0112548 A1    8/2002   Dong et al.
2003/0024323 A1    2/2003   Wang et al.

FOREIGN PATENT DOCUMENTS

| JP | 6-331506 | A | | 12/1994 |
| --- | --- | --- | --- | --- |
| JP | 8-153130 | A | | 6/1996 |
| JP | 11-258073 | A | | 9/1999 |
| JP | 11258073 | | * | 9/1999 |
| JP | 2002-35986 | A | | 2/2002 |
| JP | 2002035986 | | * | 2/2002 |
| JP | 2003-149130 | A | | 5/2003 |
| JP | 2003149130 | | * | 5/2003 |

OTHER PUBLICATIONS

Frederic Cugnon et al. "Error Assessment and Adaptivity.in Finite Element",. European Workshop on Computational mechanics, Mar. 29-30, 2001.*

"Method of Fatigue Life Estimation for Spot-Welded Structures", Yuji Nakahara et al., Society of Automotive Enineers, Inc., 2000, pp. 1-13.

Niekamp, R. et al., "The Hierarchically Graded Multilevel Finite Element Method—A New Approach to Combine the h- and the p-method Using Multilevel Graded Ansatz-Spaces," Computational Mechanics, Apr. 2001, pp. 302-304, vol. 27, No. 4, Springer, Germany.

Goldak J. et al., Computational weld mechanics, Department of Mechanical and Aeronautical Engineering, Carleton University, Ottawa, Canada, K1S 5B6, Engineering Mechanics Research Inc., Troy, Michigan, USA.

* cited by examiner

FIG. 4(a)
PRODUCTION OF PLANE DATA FOR ANALYSIS

OFFSET FOR PLATE THICKNESS REQUIRED

FIG. 4(b)
ELEMENT DIVISION

FIG. 4(c)
PRODUCTION OF NODAL POINT AT SPOT POINT POSITION

33: SPOT POINT

FIG. 4(d)
RE-DIVIDE PORTION AROUND SPOT POINT

RIGID ELEMENT

FIG. 4(e)
COUPLE PARTS USING ELEMENT

EVALUATION METHOD AND EVALUATION APPARATUS FOR SPOT WELDED PORTION

This Non-provisional application claims priority under 35U.S.C. §119(a) on Patent Application No(s). 2003-146373 and 2003-146374 filed in Japan on May 23, 2003, the entire contents of which are hereby incorporated by reference.

BACKGROUND OF THE INVENTION

1) Field of the Invention

This invention relates to a technique for evaluation after estimating, by a numerical analysis, the strength at a spot welded portion of a structure formed from a plurality of panels spot welded at a plurality of locations such as, for example, the body of an automobile.

2) Description of the Related Art

In recent years, a technique for numerically analyzing the strength of a structure using a computer has been developed and utilized in order to satisfy such demands as a demand for reduction of the period of development of a structure and a demand for reduction of the cost for development. It is known that the finite element method is useful as such a technique for an analysis of the strength of a structure as just described.

A structure is sometimes formed from a plurality of panels spot welded to each other at a plurality of locations, for example, like the body of an automobile. In order to use a computer to analyze the strength of a structure of the type just described, a spot welded portion is modeled, and the finite element method is applied to the model. Several methods have been developed for modeling a spot welded portion so as to allow the finite element to be used for the calculation, and for example, a beam coupling model, a shared nodal point model, a cobweb model, an RBE3 model, a solid model and a shared side model are known.

Figure 11A:
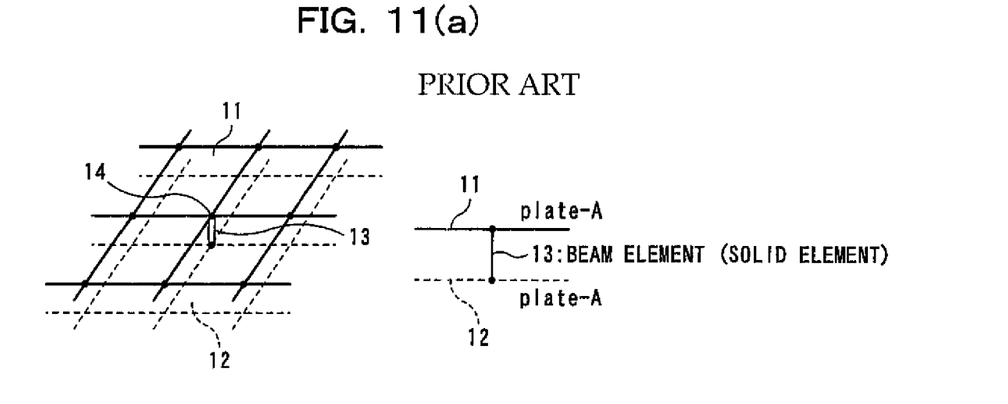
FIGS. 11(a) to 11(c) are schematic perspective views illustrating different manners of element division of a panel for conventional evaluation of a spot welded portion.
Figure 11B:
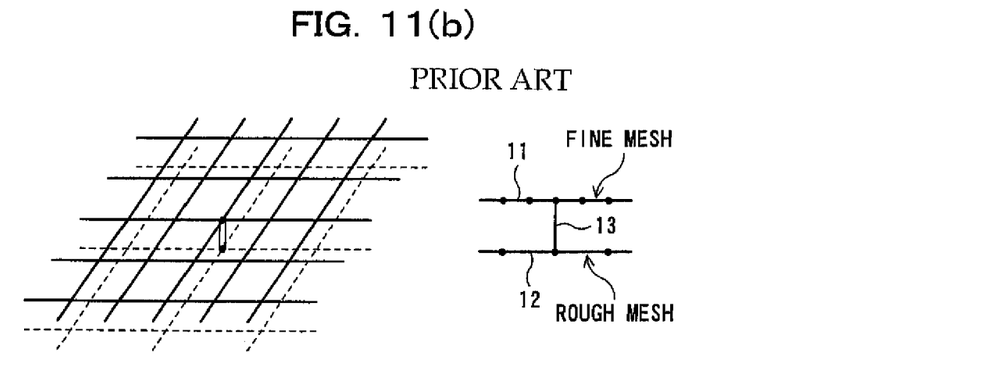
Figure 11C:
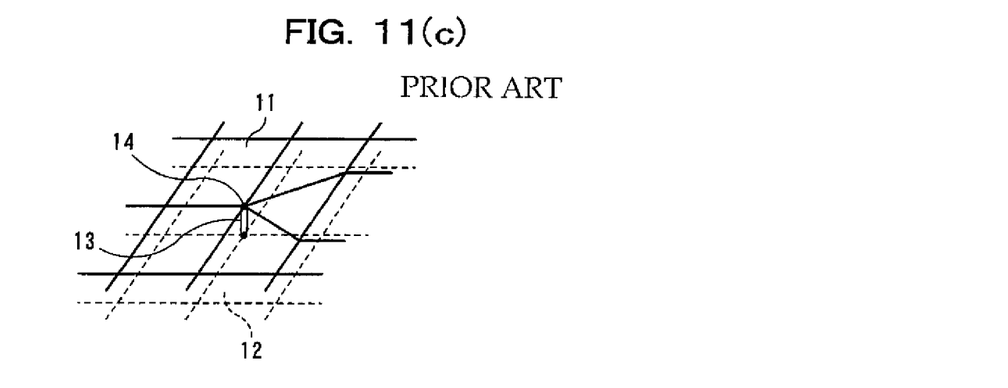

FIGS. 11(a) to 11(c) show different examples of a beam coupling model. Referring to FIGS. 11(a) to 11(c), each of the beam coupling models shown is obtained by modeling a plurality of panels 11 and 12 as being coupled to each other at a spot welded location by a beam element 13. Each of the panels 11 and 12 coupled to each other by the beam element 13 is suitably divided into elements, and the finite element method is used to perform an analysis with regard to the strength in a unit of an element obtained by the division. At this time, each of the beam element 13 and the portions of the panels 11 and 12 coupled to the beam element 13 is generally handled as a solid element.

Incidentally, according to the modeling methods mentioned above, in order to allow accurate description of an event wherein a solidified portion formed across a plurality of panels by welding transmits a bending moment from one to another one of the panels, the configuration of the model must be complicated, and much time is required for production of the model. On the contrary, if the configuration of the model is simplified so as to allow the model to be produced in a short period of time, then an event around a spot welded portion cannot be analyzed accurately.

Therefore, techniques have been developed wherein a fine model is formed for each location for which a high degree of analysis accuracy is required while a rough model is formed for any other portion so that an event around a spot welded portion can be analyzed accurately while the time required for modeling is reduced.

For example, a technique is proposed in a Patent Document 1[Japanese Patent Laid-Open No. 2002-35986] wherein a shared nodal point model is used to produce a simple model of a spot welded portion and is used to execute the finite element method, and thereafter, a value corresponding to a peeling distance in a direction perpendicular to the plane is calculated and then compared with a predetermined value to select a location at which the peeling distance is comparatively great and then a detailed model is produced for the selected location. In short, although a simple model having a low degree of analysis accuracy is used, since a great peeling distance is calculated at a spot welded location at which the degree of danger is high while a small peeling distance is calculated at another location at which the degree of danger is low, it can be discriminated accurately whether or not a detailed model is required depending upon the peeling distance.

Incidentally, when each of panels of a beam coupling model is divided into elements, various dividing manners are available as seen in FIGS. 11(a) to 11(c). In particular, the panels 11 and 12 may be divided into similar elements (usually rectangular elements) using a portion of each of the panels 11 and 12 coupled to the beam element 13 as a nodal point 14 as seen in FIG. 11(a). Or, the panels 11 and 12 may be divided into elements of different sizes from each other using a portion of each of the panels 11 and 12 coupled to the beam element 13 as a nodal point 14 as seen in FIG. 11(b). Or else, depending upon the shape of a portion around a spot welded portion, a mesh element of a different shape may be formed partially in the same panel 11 as seen in FIG. 11(c).

Where attention is paid to such manners of element division as described above, in order to reduce the time required for modeling while making it possible to accurately analyze an event around a spot welded portion as described above, since it is apparent that the danger in strength is high at a portion around a spot welded location, it is a generally possible idea to apply fine division to locations around spot welded locations while rough division is applied to the other portions.

Further, where it is tried to evaluate the strength of a panel including spot welded locations, various methods including, for example, a method wherein a stress intensity factor $\Delta K\theta$-max (K value) of the fracture mechanics is used assuming a spot welded portion as an annular crack and another method wherein a nominal structural stress $\sigma M$ of a welding nugget portion determined using the elastic theory of a flat plate from six components of force of a spot element are available.

Incidentally, where the strength of a panel including a spot welded location is evaluated using arithmetic operation performed using a computer, it is a subject to be solved what analysis technique should be adopted and what division should particularly be adopted in the proximity of a welded location in order to achieve both of assurance of the accuracy in analysis and simplification of a model.

Where the method wherein a K value of the fracture mechanics described above is used in the analysis technique, if the K value can be estimated, then simplification of a calculation model can be achieved. However, in order to estimate the K value, a database which includes data of the K value for different modes of shearing, peeling and plane bending is required, and much time and labor are required for production of the database.

On the other hand, in the method which uses the nominal structure stress $\sigma M$, although the number of elements is small and it is easy to examine a modified structure, the method is liable to be influenced by the difference in the input form, and the result of the analysis is liable to suffer from a significant dispersion.

As regards the division of elements, the cobweb model wherein a spot welded portion is described with a beam element, neighboring plate elements disposed in a fine density around the beam element and an element (for example, a solid element) having a rigidity higher than the other locations and positioned between the beam element and the neighboring plate elements for connecting them to each other is considered suitable as disclosed in the Patent Document 1 mentioned hereinabove. However, for example, where a stress value is used to perform an analysis, since those of the neighboring plate elements which are connected to the element having a higher rigidity than the other locations have stress values much higher than the other locations, the numerical analysis itself becomes difficult, and also the evaluation of a result of the analysis becomes difficult.

Further, for example, where a stress value is used to perform an analysis, it is necessary to perform the analysis in such a manner that a spot welded portion to which the cobweb model is applied and general elements neighboring the spot welded portion may be continuous to each other. In this instance, it is demanded to simplify element division as far as possible while the accuracy in analysis is assured.

SUMMARY OF THE INVENTION

It is an object of the present invention to provide an evaluation method and an evaluation apparatus for a spot welded portion by which the strength of a panel including spot welded portions can be evaluated with a high degree of accuracy while the accuracy in analysis is assured and a simplified analysis model is used.

In order to attain the object described above, according to an aspect of the present invention, there is provided an evaluation method for a spot welded portion for evaluating the strength of a welded portion of a plurality of panels joined together by spot welding, comprising a first step of dividing each of the panels into a plurality of elements, a second step of calculating a stress value at the welded portion of each of the panels by a stress analysis according to a finite element method using the elements obtained by the first step, and a third step of evaluating the strength of the welded portion based on the stress value at the welded portion obtained by the second step, the first step being configured such that a portion in the proximity of the spot welded portion is divided, with a central portion of the spot welded portion registered with a nodal point of the elements, into a central element and a plurality of concentric ring-like elements including first and second ring-like elements from the center side provided by the central portion of the spot welded portion, whereafter the plural concentric ring-like elements are individually divided in a circumferential direction each into a plurality of portions to form the elements, the second step being configured such that the analysis is performed assuming the central element corresponding to the central portion of the spot welded portion as an element having a rigidity higher than the other locations, the third step being configured such that the strength of the welded portion is evaluated based on the stress value of the second ring-like element.

Where the stress analysis is performed assuming the central element corresponding to the central portion of the spot welded portion as an element having a rigidity higher than the other locations, although evaluation of the strength of the first ring-like element which neighbors directly with the central element becomes difficult because the stress at a contacting portion of the first ring-like element with the central element becomes very high when compared with the other locations, since the stress value at the second ring-like element which is an element positioned on the outer side of the first ring-like element becomes a value corresponding to the spot welded portion, the strength evaluation of the welded portion can be performed readily and with a high degree of accuracy.

Preferably, the outer diameter of the central element is set a little smaller than the outer diameter of a nugget portion of the spot welded portion, and the outer diameter of the first ring-like element is set substantially equal to the outer diameter of the nugget portion of the spot welded portion. With the configuration, the second ring-like element which is an object of evaluation can be made correspond to a circumferential edge of an actual nugget portion, and the accuracy in analysis of the evaluation object portion can be improved to assure the accuracy in evaluation.

Preferably, the width of the second ring-like element in a diametrical direction is set to a size substantially equal to a strain detection width of a strain gauge. With the configuration, by mounting a strain gauge at a portion of an actual panel corresponding to the second ring-like element to perform a test, a result of the stress analysis at the second step can be verified appropriately with a high degree of accuracy.

Preferably, each of the plural concentric ring-like elements is divided into 4 to 8 portions in the circumferential direction. Particularly, if the number of divisions in the circumferential direction is set lower than four, then the accuracy in analysis at the second step becomes excessively low, but even if the number of divisions in the circumferential direction is increased above eight, the accuracy in analysis at the second step increases only a little. Therefore, it is preferable to set the number of divisions in the circumferential direction to four to eight. Where the division number is set in this manner, the accuracy in analysis at the second step can be improved while the number of man-hours in element division at the first step is suppressed.

Preferably, the elements are formed as rectangular elements except those which are in the proximity of the spot welded portion. With the configuration, division logics at the first step can be simplified and can be easily made ready also for strength evaluation of a panel having a shape comparatively proximate to a rectangular shape such as the body of an automobile.

According to another aspect of the present invention, there is provided an evaluation method for a spot welded portion for evaluating the strength of a welded portion of a plurality of panels joined together by spot welding, comprising a first step of dividing each of the panels into a plurality of elements, a second step of calculating a stress value at the welded portion of each of the panels by a stress analysis according to a finite element method using the elements obtained by the first step, and a third step of evaluating the strength of the welded portion based on the stress value at the welded portion obtained by the second step, the first step being configured such that a portion in the proximity of the spot welded portion is divided, with a central portion of the spot welded portion registered with a nodal point of the elements, into a plurality of concentric ring-like elements around the central portion, whereafter the plural concentric ring-like elements are further divided in a circumferential direction each into a plurality of portions to form the elements, the second step being configured such that, for the outermost ring-like element positioned on the most outside from among the concentric ring-like elements obtained by the division in the proximity of the spot welded portion, the stress value being calculated by a P method finite element method which uses a high-order coordinate function.

With the configuration, to the outermost ring-like element positioned on the most outside from among the concentric ring-like elements obtained by the element division in the proximity of the spot welded portion, the P method finite element method which uses a high-order coordinate function is applied. Consequently, the continuity of the element around the spot welded portion to the general elements on the outer side of the element can be assured without making the element division comparatively fine, and the accuracy in analysis of a spot welded portion can be improved while the number of man-hours in element division and the number of steps of arithmetic operation are suppressed.

Preferably, the second step is configured such that, for the elements other than the outermost ring-like element, the stress value is calculated by an H method finite element method which uses a low-order coordinate function.

With the configuration, the stress analysis can be carried out easily and plainly using general analysis logics.

Preferably, the elements are formed as rectangular elements except that which is positioned in the proximity of the spot welded portion.

With the configuration, element division logics can be simplified and can be easily made ready also for strength evaluation of a panel having a shape comparatively proximate to a rectangular shape particularly like the body of an automobile, and the evaluation in strength of a spot welded portion can be performed with a high degree of accuracy while reducing the processing time.

Preferably, the division into the plural concentric ring-like elements is performed such that the ring is divided in a radial direction from the center into three or four layers from the first layer of the innermost layer corresponding to the spot welded portion to the third or fourth layer of the outermost layer.

With the configuration, the accuracy in analysis of a spot welded portion can be improved while the number of man-hours in element division and the number of steps of arithmetic operation are suppressed, and the evaluation in strength of a spot welded portion can be performed with a high degree of accuracy while reducing the processing time.

Preferably, each of the plural concentric ring-like elements is divided into 4 to 8 portions in the circumferential direction.

With the configuration, the accuracy in analysis of a spot welded portion can be improved while the number of man-hours in element division and the number of steps of arithmetic operation are suppressed, and the evaluation in strength of a spot welded portion can be performed with a high degree of accuracy while reducing the processing time.

According to a further aspect of the present invention, there is provided an evaluation apparatus for a spot welded portion for evaluating the strength of a welded portion of a plurality of panels joined together by spot welding, comprising element dividing means for dividing each of the panels into a plurality of elements, stress analysis arithmetic operation means for calculating a stress value at the welded portion of each of the panels by a stress analysis according to a finite element method using the elements obtained by the element dividing means, and strength evaluation means for evaluating the strength of the welded portion based on the stress value at the welded portion calculated by the stress analysis arithmetic operation means, the element dividing means dividing a portion in the proximity of the spot welded portion, with a central portion of the spot welded portion registered with a nodal point of the elements, into a central element and a plurality of concentric ring-like elements including first and second ring-like elements from the center side provided by the central portion of the spot welded portion, the element dividing means further dividing the plural concentric ring-like elements individually in a circumferential direction each into a plurality of portions to form the elements, the stress analysis arithmetic operation means performing the analysis assuming the central element corresponding to the central portion of the spot welded portion as an element having a rigidity higher than the other locations, the strength evaluation means evaluating the strength of the welded portion based on the stress value of the second ring-like element.

Although evaluation of the strength of the element which neighbors directly with the central element which has a higher rigidity than the other locations becomes difficult because the stress value at the element becomes very high when compared with the other locations, since the stress value at the second ring-like element which does not neighbor directly with the central element but is positioned near to the central element becomes a value corresponding to the spot welded portion, the strength evaluation of the welded portion can be performed readily and with a high degree of accuracy.

According to a still further aspect of the present invention, there is provided an evaluation apparatus for a spot welded portion for evaluating the strength of a welded portion of a plurality of panels joined together by spot welding, comprising element dividing means for dividing each of the panels into a plurality of elements, stress analysis arithmetic operation means for calculating a stress value at the welded portion of each of the panels by a stress analysis according to a finite element method using the elements obtained by the element dividing means, and strength evaluation means for evaluating the strength of the welded portion based on the stress value at the welded portion calculated by the stress analysis arithmetic operation means, the element dividing means dividing a portion in the proximity of the spot welded portion, with a central portion of the spot welded portion registered with a nodal point of the elements, into a central element and a plurality of concentric ring-like elements including an outer ring-like element from the center side provided by the central portion of the spot welded portion, the element dividing means further dividing the plural concentric ring-like elements individually in a circumferential direction each into a plurality of portions to form the elements, the stress analysis arithmetic operation means performing the analysis assuming the central element corresponding to the central portion of the spot welded portion as an element including an element having a rigidity higher than the other locations and having a size greater than the element having the higher rigidity, the strength evaluation means evaluating the strength of the welded portion based on the stress value of the outer ring-like element.

Where the central element corresponding to the central portion of the spot welded portion is assumed as an element including an element having a rigidity higher than the other locations and having a size greater than the element having the higher rigidity in this manner, although evaluation of the strength of the central element becomes difficult because the analyzed stress value at the central element becomes very high when compared with the other locations, since the strength of the welded portion is evaluated based on the stress value at the outer ring-like element continuous to the outside of the central element, a result of the evaluation at the spot welded portion can be obtained. Consequently, the strength evaluation of the welded portion can be performed readily and with a high degree of accuracy.

According to a yet further aspect of the present invention, there is provided a stress analysis apparatus for a spot welded portion for analyzing a stress state of a welded portion of a plurality of panels joined together by spot welding, comprising element dividing means for automatically dividing each of the panels into a plurality of elements, and stress analysis arithmetic operation means for calculating a stress value at the welded portion of each of the panels by a stress analysis according to a finite element method using the elements obtained by the element dividing means, the element dividing means dividing a portion in the proximity of the spot welded portion, with a central portion of the spot welded portion registered with a nodal point of the elements, into a plurality of concentric ring-like elements around the central portion, the element dividing means further dividing the plural concentric ring-like elements individually in a circumferential direction each into a plurality of portions to form the elements, the stress analysis arithmetic operation means applying a P method finite element method which uses a high-order coordinate function to the outermost ring-like element positioned on the most outside from among the concentric ring-like elements obtained by the division in the proximity of the spot welded portion.

With the configuration, to the outermost ring-like element positioned on the most outside from among the concentric ring-like elements obtained by the element division in the proximity of the spot welded portion, the P method finite element method which uses a high-order coordinate function is applied. Consequently, the continuity of the element around the spot welded portion to the general elements on the outer side of the element can be assured without making the element division comparatively fine, and the accuracy in analysis of a spot welded portion can be improved while the number of man-hours in element division and the number of steps of arithmetic operation are suppressed.

The above and other objects, features and advantages of the present invention will become apparent from the following description and the appended claims, taken in conjunction with the accompanying drawings in which like parts or elements denoted by like reference symbols.

DETAILED DESCRIPTION OF THE INVENTION

FIGS. 1 to 9 illustrate an evaluation method and an evaluation apparatus (including a stress analysis apparatus) for a spot welded portion according to an embodiment of the present invention, and the embodiment of the present invention is described below with reference to FIGS. 1 to 9.

Figure 2:
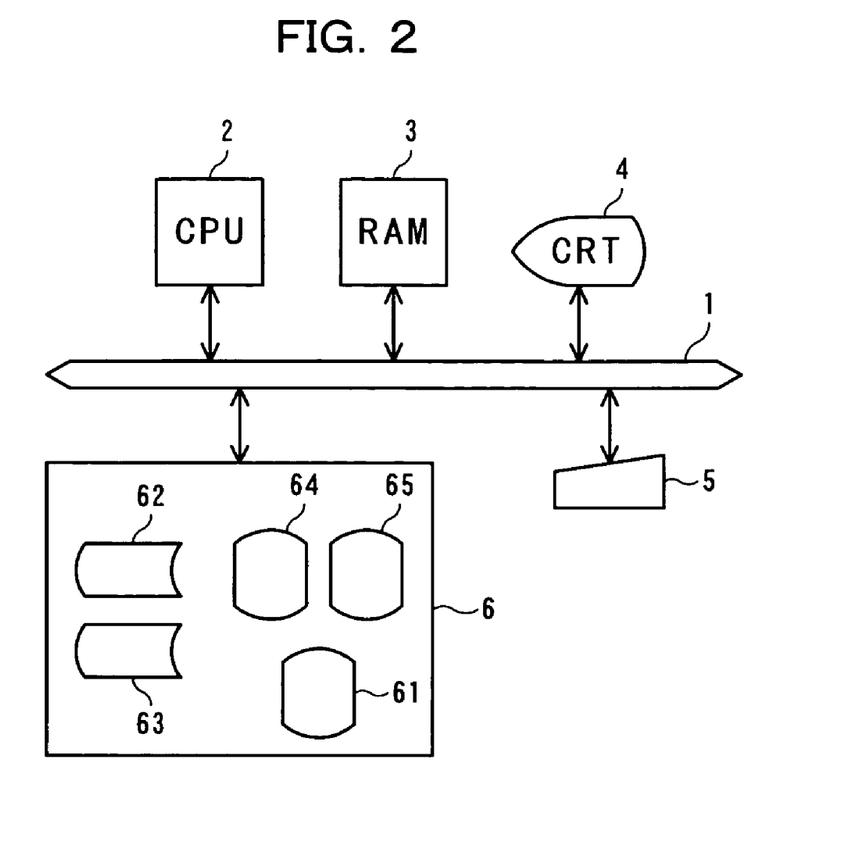
FIG. 2 is a block diagram showing a hardware configuration of the evaluation apparatus for a spot welded portion according to the embodiment of the present invention.
Figure 3:
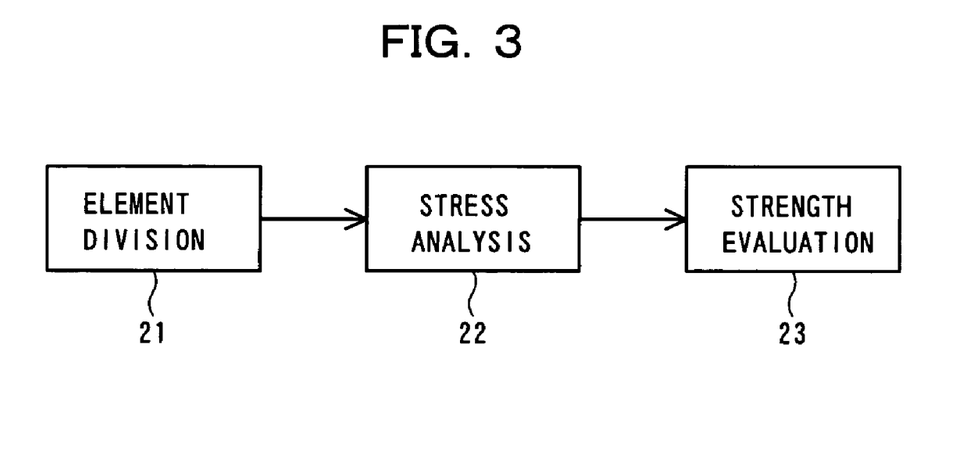
FIG. 3 is a block diagram showing a functional configuration of the evaluation apparatus for a spot welded portion according to the embodiment of the present invention.

Referring first to FIG. 2, a hardware configuration of the evaluation apparatus according to the present embodiment is shown in block diagram. The evaluation apparatus includes a CPU 2, a RAM 3, a display unit (here in the form of a CRT) 4, a keyboard 5, and a disk apparatus 6 connected to each other by a common bus 1. The CPU 2 is a central processing unit for executing an operation program file 61 stored in the disk apparatus 6 on the RAM 3. Also a CAD data file 62 for a structure (here, the body of an automobile) of an object of an analysis, an analysis result file 63 of the structure obtained by the finite element method (hereinafter referred to as FEM), a panel structure file 64 produced by operation of the present apparatus, a stress data file 65 and other necessary files are stored suitably into the disk apparatus 6.

The present evaluation apparatus uses such a hardware configuration as described above to implement, as shown in FIG. 3, a function (element division means) 21 for automatically dividing the structure of the evaluation object into a plurality of elements (also called meshes or mesh elements), another function (stress analysis arithmetic operation means) 22 for calculating a stress value of a welded portion of the panel by a stress analysis using the FEM, and a further function (strength evaluation means) 23 for evaluating the strength of the welded portion based on the calculated stress value of the welded portion. The functions 21 to 23 can be implemented making use of existing program software.

While the evaluation method for a spot welded portion according to the present invention is described, also the present evaluation apparatus is described.

Figure 1:
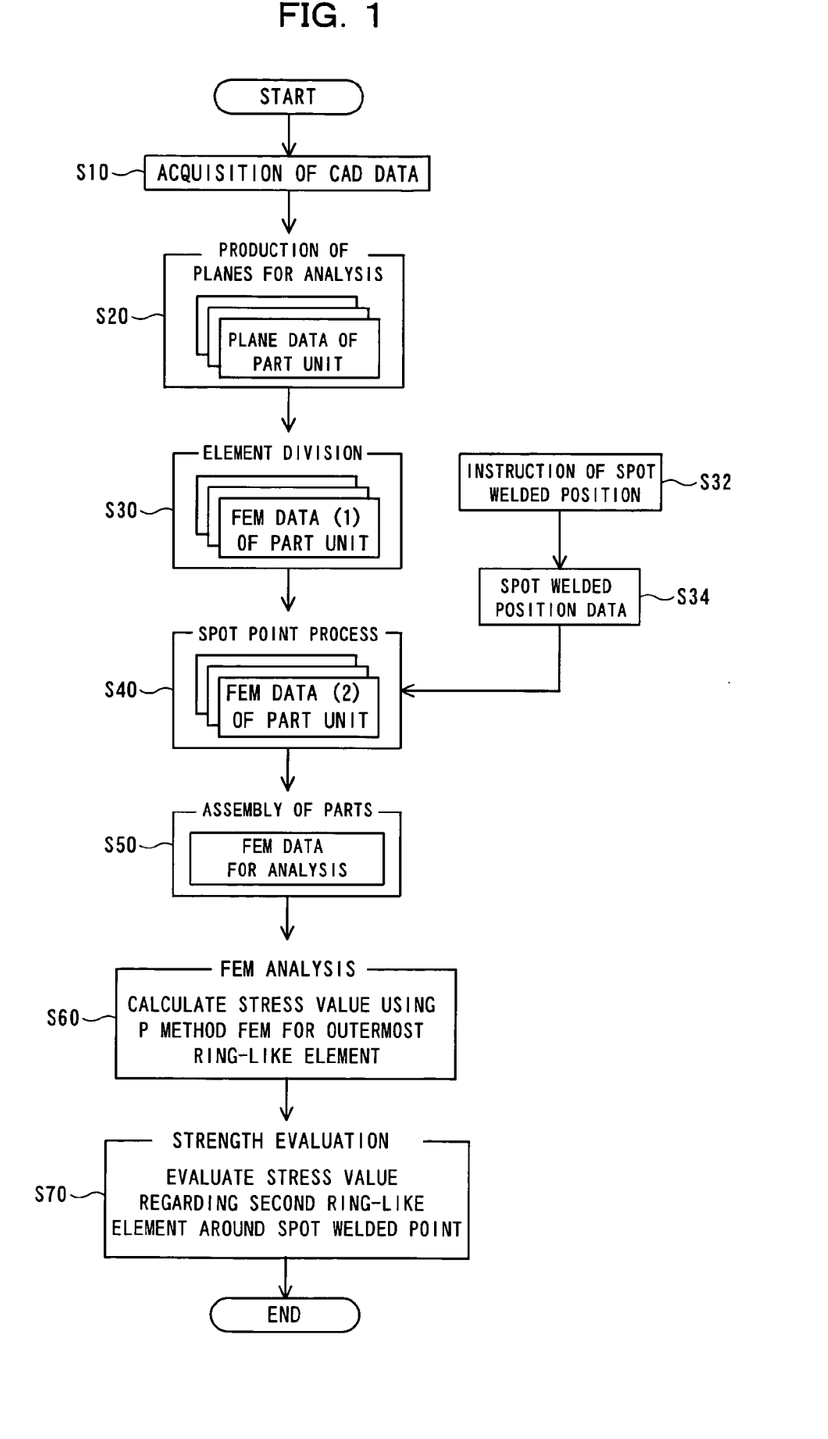
FIG. 1 is a flow chart illustrating an evaluation method and operation of an evaluation apparatus for a spot welded portion according to an embodiment of the present invention.

Referring now to FIG. 1, according to the present evaluation method, CAD data are acquired first (step S10), and then plane data for analysis are produced based on the CAD data (step S20). Here, the plane data are produced as plane data of a part unit which composes the structure (body of the automobile) [plane data 31 of a unit of a body panel of the automobile, refer to FIG. 4(a)]. Thereupon, offsetting by an amount equal to the plate thickness and so forth are performed as occasion demands.

Then, element division is performed at steps S30 and S40 by the element division means 21.

In particular, the element division means 21 performs element division of the plane data in a unit of a part to produce first FEM data 32 (step S30). The element division is performed such that each element may have a principally rectangular shape [refer to FIG. 4(b)]. While such simple rectangular element division can make the division logic comparatively simple, where the object of element division has a shape comparatively proximate to a plane and comparatively proximate to a rectangular shape like an automobile panel, not only the division logic is simple but also the affinity between the elements and the panel shape is good.

Meanwhile, an instruction of the position of a spot welded portion is issued (inputted) in parallel to the acquisition of the CAD data (step S32). Thus, spot welded position data is produced based on the inputted position of the spot welded portion (step S34). Then, based on the spot welded position data, a special process (spot point process) is performed for those of the first FEM data produced at step S30 which are positioned around the spot welded point (step S40).

Figure 4A:
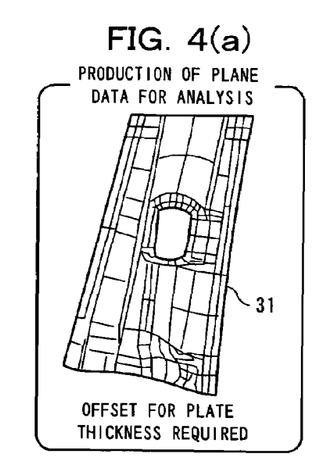
FIGS. 4(a) to 4(e) are schematic views illustrating data processing of a panel according to the embodiment of the present invention and particularly illustrating an example of processing data of the panel at different steps.
Figure 4B:
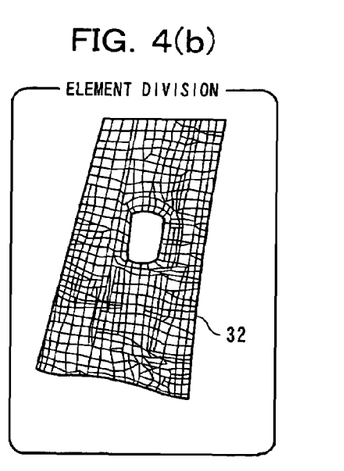
Figure 4C:
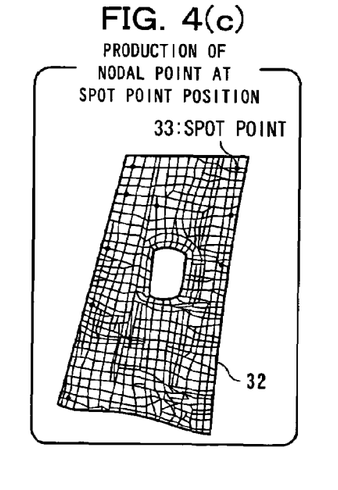
Figure 4D:
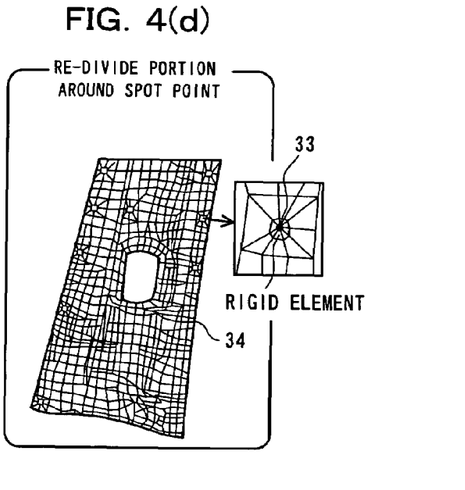

In particular, a nodal point 33 is produced based on the first FEM data, that is, the panel data obtained by the automatic element division, in accordance with the spot welded position (also referred to as spot welded point or merely as spot point) as seen in FIG. 4(c), and a portion around the nodal point 33 (around the spot welded point) is re-divided to produce second FEM data 34 [refer to FIG. 4(d)]. According to the present method and apparatus, a unique process is performed in the re-division as hereinafter described.

Figure 4E:
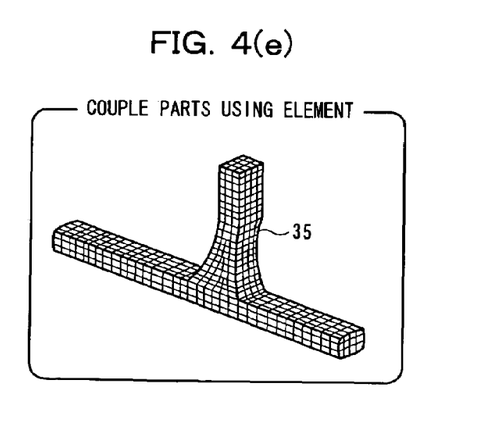

After the second FEM data 34 are produced in a unit of apart in this manner, the parts are assembled by coupling them at such spot welded locations each by a beam element [refer to FIG. 4(e)] to produce FEM data 35 for analysis (step S50).

Then, the FEM data 35 for analysis are inputted to the stress analysis arithmetic operation function 22 so that the stress analysis arithmetic operation function 22 calculates stress values at individual portions (particularly the welded portions) of the panels by a stress analysis according to the finite element method in a unit of an element (step S60). Thereupon, the arithmetic operation is performed assuming the re-divided region of the nodal point 33 (spot welded point region) as a rigid element. Further, the P method FEM is used to perform an analysis for an outermost ring-like element from among the elements around the nodal point 33 assuming the outermost ring-like element as a P method element while the general H method FEM is used to perform an analysis for the other elements.

It is to be noted that the stress values calculated here are those, for example, with respect to tensile shear, pure shear, cross tension, in-plane bend, in-plane twist and so forth and are set so that the stress where force applied to the actual structure is simulated is calculated.

After the stress values at the individual portions are calculated in this manner, the strength of each of the welded portions is evaluated by the strength evaluation function 23 based on the stress value of a second ring-like element which does not neighbor directly but neighbors with the rigid element through a first ring-like element around the spot welded point (step S70).

Here, a method of re-dividing a portion around the center of a spot welded point determined as a nodal point 33 (around the spot welded point) is described.

Figure 5A:
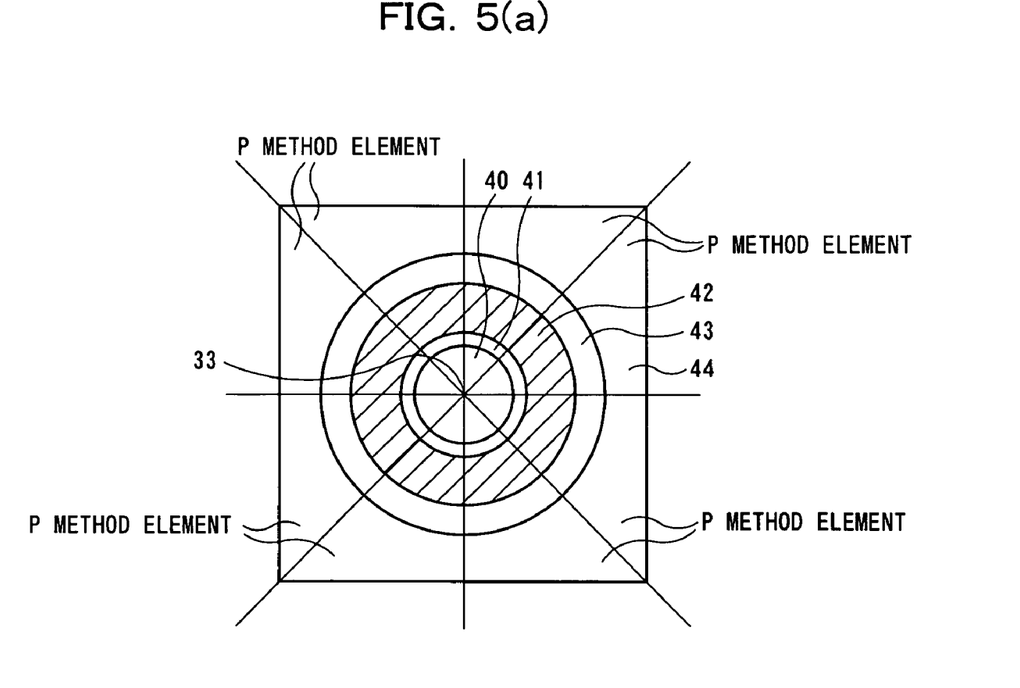
FIG. 5(a) is a schematic view illustrating element division of a spot welded portion according to the embodiment of the present invention and FIG. 5(b) is a schematic perspective view illustrating the element division of the spot welded portion according to the embodiment of the present invention.

As shown in FIG. 5(a), a portion of a panel in the proximity of a spot welded point is divided concentrically around the center of the spot welded point in order in a diametrical direction from the center into a central element 40, a first ring-like element (first layer) 41, a second ring-like element (second layer) 42, a third ring-like element (third layer) 43, and an outermost ring-like element (fourth layer) 44. Further, each of the first ring-like element 41, second ring-like element 42, third ring-like element 43 and fourth ring-like element (outermost ring-like element) 44 is divided into eight portions in a circumferential direction.

Figure 5B:
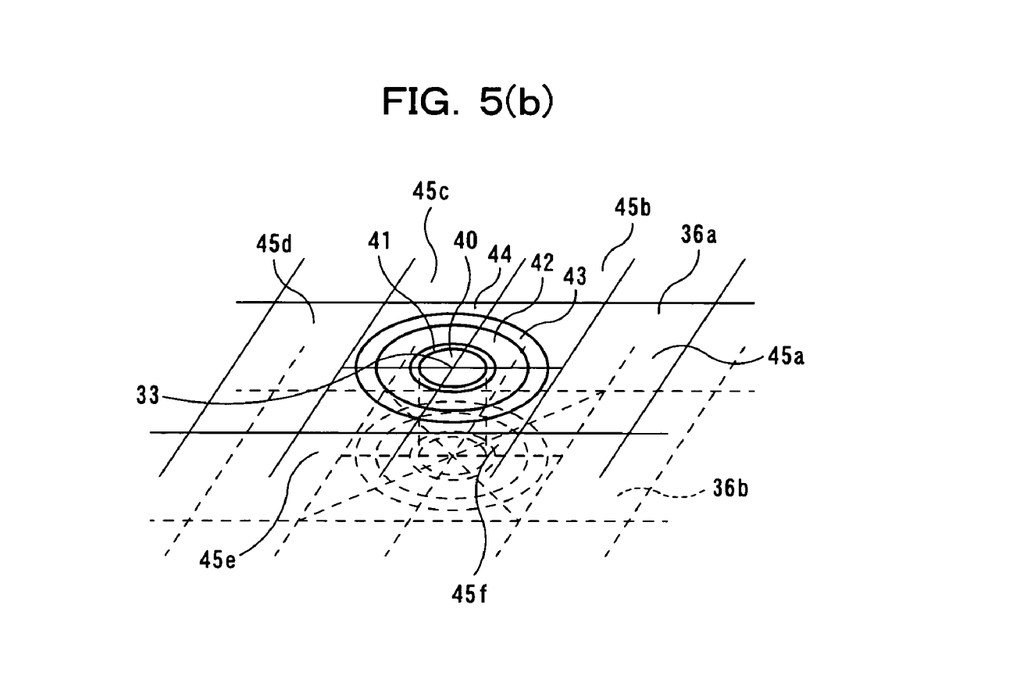

As a result, eight first ring-like elements 41 directly neighboring with the central element 40, eight second ring-like elements 42 individually directly neighboring with the outer side of the first ring-like elements 41, eight third ring-like elements 43 individually directly neighboring with the outer side of the second ring-like elements 42, and eight outermost ring-like elements 44 individually directly neighboring with the outer side of the third ring-like elements 43 are formed around the spot welded point. As shown in FIG. 5(b), such element division as just described is performed for each of a plurality of panels 36a and 36b (where the panels need not be distinguished from each other, reference numeral 36 is used for each panel) to be coupled by a beam element provided as the spot welded portion.

Figure 6A:
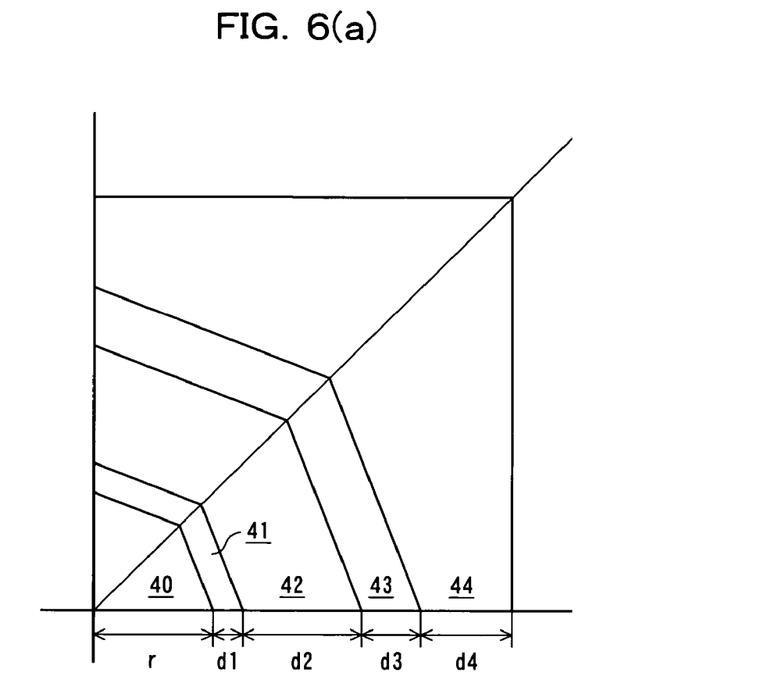
FIG. 6(a) is a diagram showing elements obtained by division of a spot welded portion according to the embodiment of the present invention and illustrating an analysis of a stress at each of the elements and a strength evaluation of the spot welded portion.
Figure 6B:
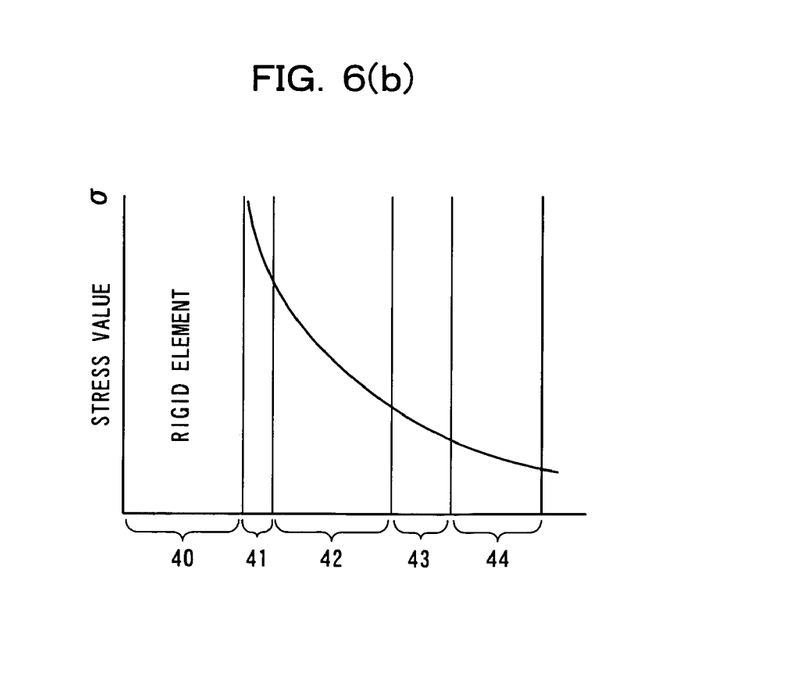
FIG. 6(b) is a graph schematically showing a stress value characteristic of the elements and illustrating the stress analysis at the elements obtained by division of the spot welded portion according to the embodiment of the present invention and the strength valuation of the spot welded portion.

Incidentally, FIG. 6(a) is a diagrammatic view showing ¼ the totaling elements around the spot welded point, and FIG. 6(b) diagrammatically illustrates a stress value characteristic regarding the elements 41 to 44.

When a stress value analysis is performed regarding the central element 40 as a rigid element, the stress value σ indicates a value which decreases as the distance from the central element 40 increases but increases as the distance to the central element 40 decreases as seen in FIG. 6(b). Accordingly, at one end of the first ring-like element 41 directly neighboring with the central element 40, the stress value σ exhibits a very high value when compared with those at the other locations and cannot be calculated unless complicated approximate calculation is performed, and depending upon the approximation method, there is the possibility that also the evaluation based on the stress may become inappropriate.

Therefore, in the present technique, the stress value of the first ring-like element 41 is eliminated from the object of the intensity evaluation, but the intensity evaluation is performed based on the stress value of the second ring-like element 42 continuous to the first ring-like element 41.

Incidentally, as seen in FIG. 6(a), the radial length (radius) of the central element 40 is set to r; the radial length (outer radius-inner radius) of the first ring-like element 41 to d1; the radial length (outer radius-inner radius) of the second ring-like element 42 to d2; the radial length (outer radius-inner radius) of the third ring-like element 43 to d3; and the radial length (outer radius-inner radius) of the outermost ring-like element 44 to d4.

Figure 9:
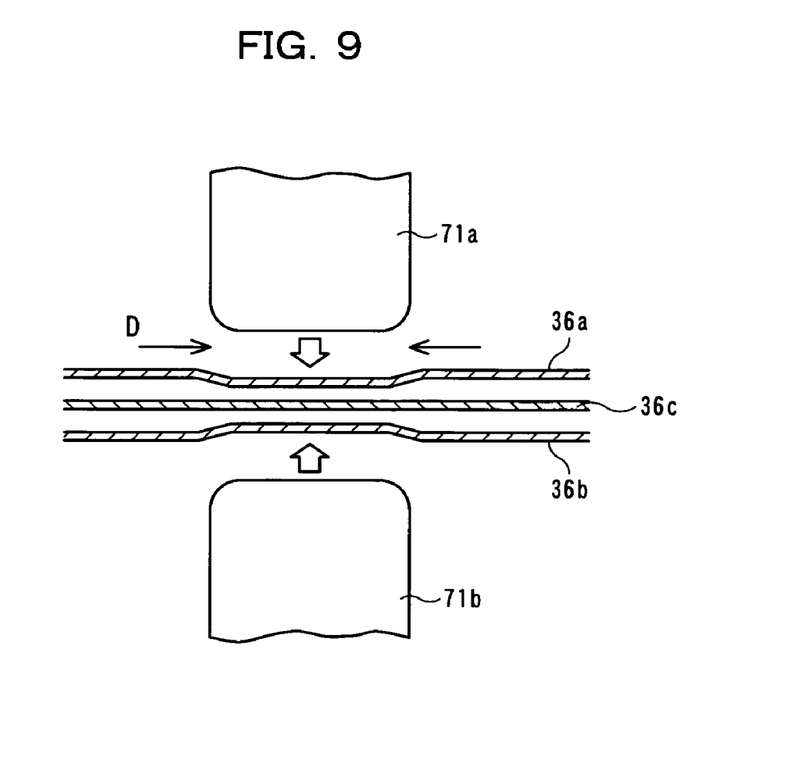
FIG. 9 is a schematic sectional view of the actual vehicle panel showing the spot welded portion according to the embodiment of the present invention.

The settings in magnitude in the radial direction of the central element 40 and the first ring-like element 41 correspond to the outer diameter D of the nugget of the spot welded portion. In particular, in spot welding, a nugget is formed on panels 36a, 36b and 36c so as to correspond to the outer diameter of welding guns 71a and 71b as seen in FIG. 9. Although the outer diameter r of the central element 40 handled as a rigid element should originally be made coincide with the outer diameter D of the nugget, since, according to the present technique, the strength evaluation is performed taking notice of the second ring-like element 42, in order to make the second ring-like element 42 coincide with the circumference of the nugget, the sum r+d1 of the dimensions in the diametrical direction of the central element 40 and the first ring-like element 41 is set so as to substantially coincide with the outer diameter D of the nugget.

Consequently, the dimension d1 of the first ring-like element 41 in the diametrical direction can be suppressed and the accuracy in analysis can be assured.

Figure 7:
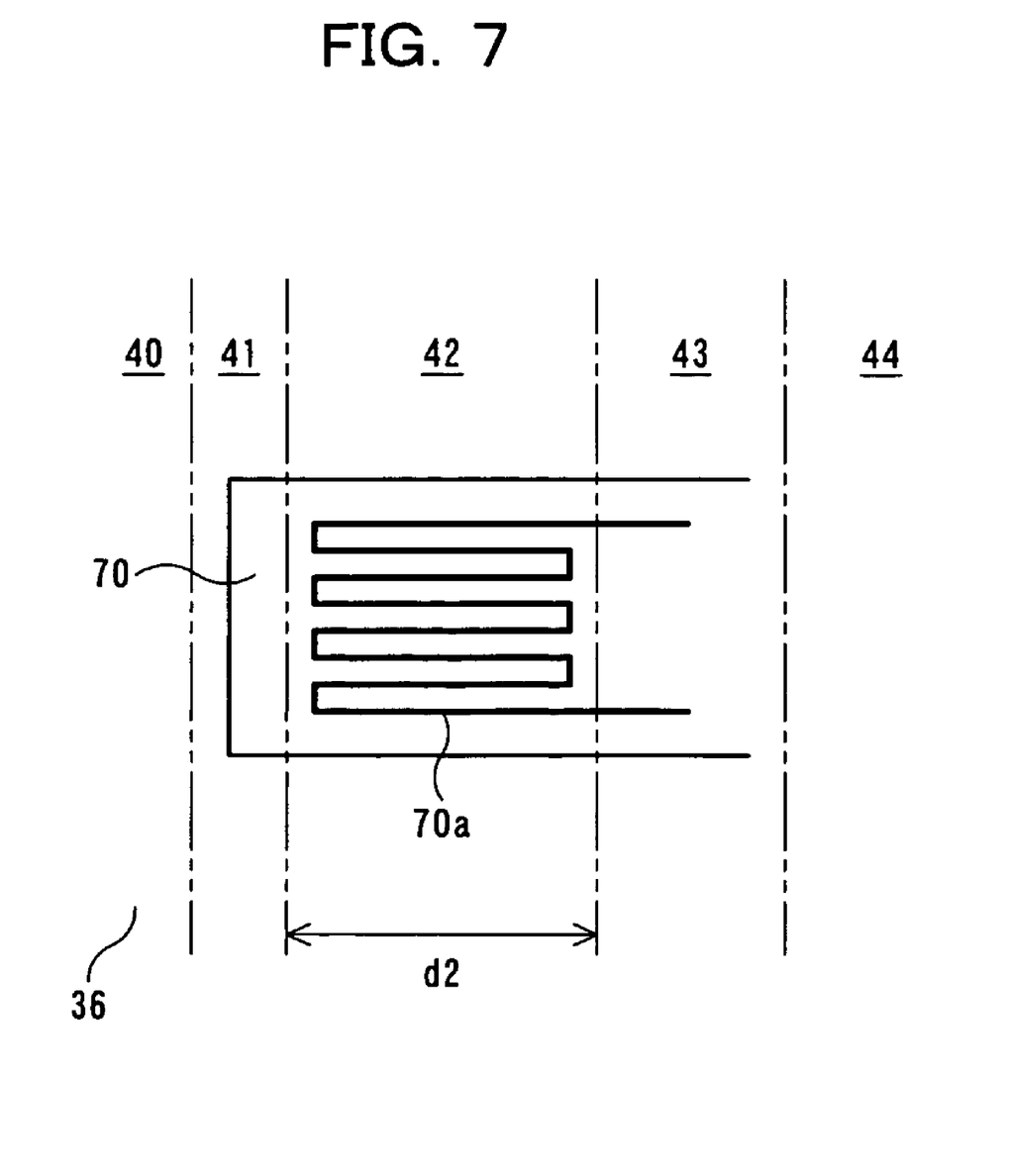
FIG. 7 is a schematic plan view illustrating an actual vehicle test according to the embodiment of the present invention and showing a strain gauge mounted on a spot welded portion of an actual vehicle.

Further, the radial length d2 of the second ring-like element 42 is set so as to correspond to a strain detection value of an existing strain gauge. In particular, if a strain gauge 70 can be mounted just at a location of a panels 36 of an actual machine (actual vehicle) corresponding to the second ring-like element 42, then a stress analysis result can be verified appropriately with a high degree accuracy by performing an actual machine test. Therefore, the radial length d2 of the second ring-like element 42 is set so as to correspond to a strain detection width of a sensor portion 70a of the strain gauge 70.

Further, in the present technique, the third ring-like element 43 and the outermost ring-like element 44 are provided on the outer side of the second ring-like element 42 which is an object of evaluation, and the P method FEM is applied to the outermost ring-like element 44 regarding the same as a P method element while the H method FEM is applied to the other elements.

Since the third ring-like element 43 is provided so as to connect the second ring-like element 42 which is an object of evaluation and the outermost ring-like element 44 to which the P method FEM is applied to each other smoothly, there is no necessity to provide the third ring-like element 43 with a very great length in the radial direction (outer radius-inner radius). Therefore, the accuracy in analysis is raised by setting the length of the third ring-like element 43 in the radial direction to a comparatively low value.

Figure 8:
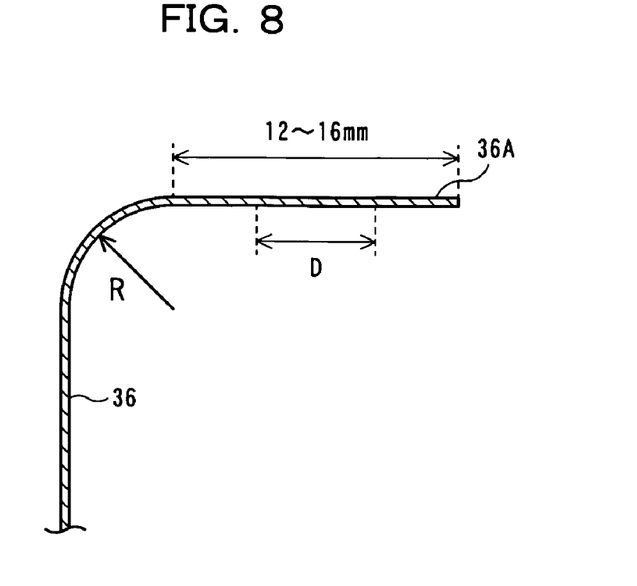
FIG. 8 is a schematic sectional view of an actual vehicle panel illustrating the actual vehicle test according to the embodiment of the present invention and showing the strain gauge mounted on the spot welded portion of the actual vehicle.

On the other hand, the outer radius of the elements around the spot welded portion (that is, the outer radius of the outermost ring-like element 44) is restricted by the flange width of a flange portion which is provided at many welded locations. In particular, a panel 36 to be spot welded has many such flange portions 36A as shown in FIG. 8, and the flange width (except a portion indicated by R) of such a flange portion 36A as just mentioned usually ranges approximately from 12 to 16 mm.

In conformity with this, according to the present technique, the outer radius of the elements around the spot welded point (the distance from the center to the outermost portion) is set to approximately 12 to 16 mm.

Figure 10A:
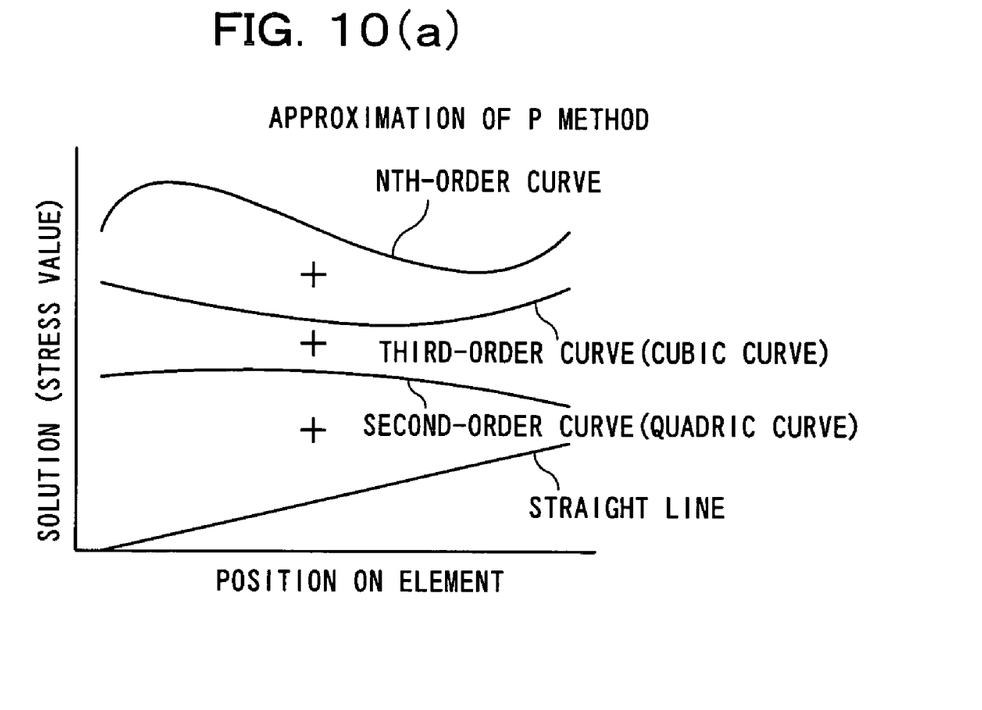
FIG. 10(a) is a diagram illustrating a P method finite element method according to the embodiment of the present invention and FIG. 10(b) is a diagram illustrating a conventional H method finite element method for comparison with the P method finite method according to the embodiment of the present invention.
Figure 10B:
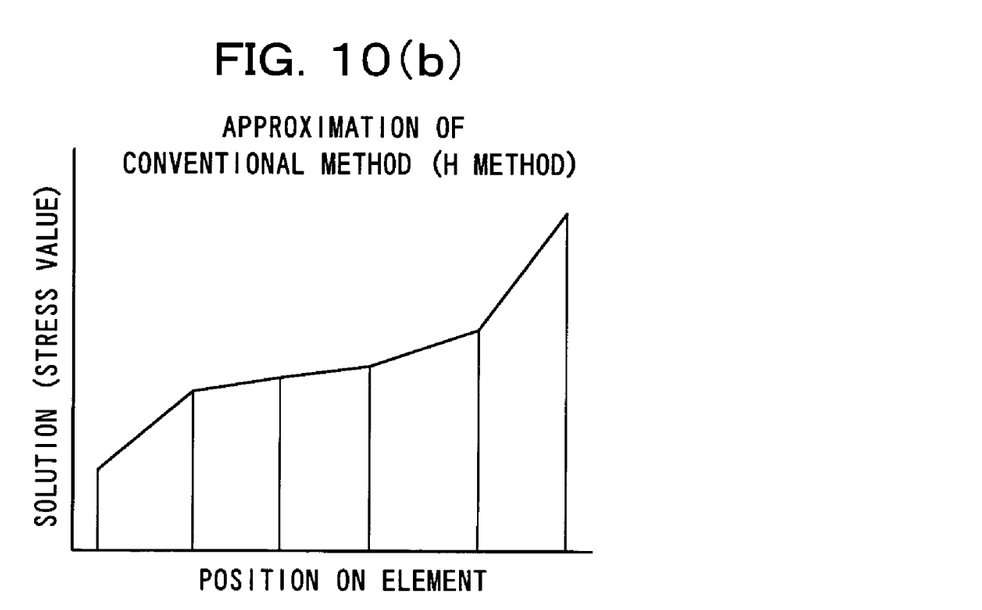

As a result, although the radial length d4 of the outermost ring-like element 44 becomes comparatively large, the accuracy in analysis is assured sufficiently. In particular, to the analysis of the outermost ring-like element 44, the P method FEM is applied as described hereinabove in order to assure the continuity thereof to the general elements 45a to 45f [refer to FIG. 5(b)] on the outer side of the re-divided elements around the spot welded point. In the P method FEM, by adopting a stress analysis of a high-order number according to a high-order function (high-order coordinate function) as seen in FIG. 10(a), an analysis of a high degree of accuracy can be performed while comparatively large elements are used without finely dividing the elements as in the H method illustrated in FIG. 10(b) [a technique which adopts a stress analysis of a low-order number according to a low-order function (low-order coordinate function)].

It is to be noted here that the high-order function adopted in the P method FEM is a function of a higher order than that of a function adopted by the H method, and for example, where a function (linear function) whose maximum order number is 1 is used in the H method, the high-order function adopted by the P method FEM is a function of the second or higher order. Naturally, in order to raise the accuracy in analysis using the P method FEM, a higher-order function should be adopted.

Since the evaluation method and the evaluation apparatus (including the stress analysis apparatus) for a spot welded portion as an embodiment of the present invention are configured in such a manner as described above, they can achieve the following advantages.

Although evaluation of the strength of the first ring-like element 41 which directly neighbors with the central element 40 as a rigid element is more difficult than that of the other locations because the stress value at the first ring-like element 41 is very high when compared with those of the other locations, according to the present technique, since the strength evaluation is performed based on the stress value at the second ring-like element 42, the strength evaluation of the welded portion can be performed readily with a high degree of accuracy. In other words, since the second ring-like element 42 is near to the central element 40 although it does not directly neighbor with the central element 40 and is positioned corresponding to the circumference of the welding nugget, the strength evaluation of the welded portion can be performed readily with a high degree of accuracy.

Further, since the outer diameter of the central element 40 is set a little smaller than the outer diameter of the nugget portion of the spot welded portion and the outer diameter of the first ring-like element 41 is set substantially equal to the outer diameter of the nugget portion of the spot welded portion, the second ring-like element 42 which is an object of evaluation and the circumferential edge of the actual nugget portion can be made correspond to each other. Consequently, the accuracy in analysis of the evaluation object portion can be raised and the accuracy in evaluation can be assured.

By setting the width in the radial direction of the second ring-like element 42 to a size substantially equal to the strain detection width of the strain gauge 70, an actual vehicle test can be performed with the strain gauge mounted at a location of an actual vehicle corresponding to the second ring-like element to verify a stress analysis result by the second step appropriately with a high degree of accuracy, and the technique for strength evaluation of a spot welded portion can be improved.

Generally, in the H method FEM, element division is normally made finer to raise the accuracy in analysis, but where each of the first to fourth ring-like elements 41 to 44 is divided into four to eight portions in the circumferential direction, a sufficient degree of accuracy in analysis is achieved. Particularly, although the accuracy in analysis increases in response to an increase of the division number where the number of divisions in the circumferential direction is increased up to eight or the like, even if the number of divisions in the circumferential direction is increased above eight, the accuracy in analysis increases only a little. Therefore, it is preferable to set the number of divisions in the circumferential direction to eight. Where the division number is set in this manner, the accuracy in analysis of a spot welded portion can be improved while the number of man-hours in element division and the number of steps of arithmetic operation are suppressed, and strength evaluation of a spot welded portion can be performed with a high degree of accuracy while the processing time is reduced.

Further, also where the division of a portion in the proximity of the spot welded portion into a plurality of concentric ring-like elements is performed such that the portion is divided in radial directions from the center into four layers from the first layer of the innermost layer corresponding to the spot welded portion to the fourth layer of the outermost layer, the accuracy in analysis of the spot welded portion can be improved while the number of man-hours in element division and the number of steps of arithmetic operation are suppressed, and strength evaluation of the spot welded portion can be performed with a high degree of accuracy while the processing time is reduced.

Furthermore, since the P method FEM is applied to the outermost ring-like element 44, the continuity thereof to the general elements (principally rectangular elements) 45a to 45f on the outer side of the re-divided element around the spot welded point can be assured without making the element division finer, and the accuracy in analysis of the spot welded portion can be improved while the number of man-hours in element division and the number of steps of arithmetic operation are suppressed.

Further, since the stress value at each of the elements other than the outermost ring-like element is calculated by the H method finite element method which uses a low-order stress analysis (for example, a linear stress analysis which is a first-order stress analysis), the stress analysis can be carried out simply and plainly using general analysis logics.

Further, where the elements are formed principally as rectangular elements except those in the proximity of each spot welded portion, the element division logics can be simplified and can be easily made ready also for strength evaluation of a panel having a shape comparatively proximate to a rectangular shape such as the body of an automobile. Thus, strength evaluation of a spot welded portion can be performed with a high degree of accuracy while the processing time is reduced.

While an embodiment of the present invention has been described, the present invention is not limited to the embodiment but can be carried out in various modified forms without departing from the spirit and scope of the present invention.

For example, while, in the embodiment described above, a stress value analysis is performed assuming a central element as a rigid element, the present invention is not limited to this, but substantially similar operations and advantages to those of the embodiment described above can be achieved if a stress value analysis is performed at least assuming a central element as an element having a higher rigidity than the other elements.

Further, while the embodiment described above is configured such that a panel is divided concentrically around the center of a spot welded point in order in a diametrical direction from the center into a central element, a first ring-like element, a second ring-like element, a third ring-like element, and an outermost ring-like element, the manner of element division, the selection of an element of an object of evaluation of the strength and so forth are not limited to them, but the embodiment may be modified such that a central element is set as an element including an element having a high rigidity and having a greater size in a diametrical direction than the element having the high rigidity and a ring-like outer element (outer ring-like element) is set continuously to the outer side of the central element such that the strength of the welded portion is evaluated based on a stress value at the outer ring-like element.

Further, while, in the embodiment, a panel is divided concentrically around the center of a spot welded point in order in a diametrical direction from the center into four elements of a first ring-like element, a second ring-like element, a third ring-like element, and an outermost ring-like element around a central element, the element division is not limited to this, but a panel may be divided concentrically around the center of a spot welded point in a diametrical direction from the center otherwise into two or three elements or five or more elements. Also in this instance, substantially similar operations and advantages to those of the embodiment described above.

Preferably, the evaluation method and the evaluation apparatus are configured such that a panel is divided concentrically around the center of a spot welded portion in a diametrical direction from the center into three or four layers. Where the configuration just described is adopted, the accuracy in analysis of a spot welded portion can be improved while the number of man-hours for element division and the number of steps of arithmetic operation are suppressed.

What is claimed is:

1. An evaluation method for a spot welded portion for evaluating a strength of a welded portion of a plurality of panels joined together by spot welding, comprising:
a first step of dividing each of the panels into a plurality of elements;
a second step of calculating a stress value at the welded portion of each of the panels by a stress analysis according to a finite element method using the elements obtained by the first step; and
a third step of evaluating a strength of the welded portion based on the stress value at the welded portion obtained by the second step;
the first step being performed such that a portion in a proximity of the spot welded portion is divided, with a central portion of the spot welded portion being determined as a nodal point of the elements, into a central element and a plurality of concentric ring-like elements including first and second ring-like elements from a center side provided by the central portion of the spot welded portion, whereafter the plural concentric ring-like elements are individually divided in a circumferential direction each into a plurality of portions to form the elements;
the second step being performed such that an analysis being performed assuming the central element corresponding to the central portion of the spot welded portion as a rigid element;
the third step being performed such that the strength of the welded portion being evaluated based on the stress value of the second ring-like element by eliminating a stress value of the first ring-like element from the evaluation, the second ring-like element neighboring the central portion through the first ring-like element;
wherein an outer diameter of the central element is set smaller than an outer diameter of a nugget portion of the spot welded portion, and
the first ring-like element has an outer diameter that coincides with the outer diameter of the nugget portion, such that the second ring-like element substantially coincides with a circumferential portion of the nugget portion.

2. The evaluation method for a spot welded portion as claimed in claim 1, wherein a width of the second ring-like element in a diametrical direction is set to a size substantially equal to a strain detection width of a strain gauge.

3. The evaluation method for a spot welded portion as claimed in claim 1, wherein each of the plural concentric ring-like elements is divided into 4 to 8 portions in the circumferential direction.

4. The evaluation method for a spot welded portion as claimed in claim 1, wherein the elements are formed as rectangular elements except those which are in the proximity of the spot welded portion.

5. An evaluation method for a spot welded portion for evaluating a strength of a welded portion of a plurality of panels joined together by spot welding, comprising:
a first step of dividing each of the panels into a plurality of elements;
a second step of calculating a stress value at the welded portion of each of the panels by a stress analysis according to a finite element method using the elements obtained by the first step; and
a third step of evaluating a strength of the welded portion based on the stress value at the welded portion obtained by the second step;
the first step being performed such that a portion in a proximity of the spot welded portion is divided, with a central portion of the spot welded portion being determined as a nodal point of the elements, into a plurality of concentric ring-like elements around the central portion, whereafter the plural concentric ring-like elements are further divided in a circumferential direction each into a plurality of portions to form the elements;

the second step being performed such that only for an outermost ring-like element positioned on a most outside from among the concentric ring-like elements obtained by the division in the proximity of the spot welded portion, the stress value being calculated by a P method finite element method which uses a high-order coordinate function, and the second step being configured such that, for the elements other than the outermost ring-like element and a ring-like element closest to the central portion, the stress value is calculated by an H method finite element method which uses a low-order coordinate function, wherein the ring-like element closest to the central portion has an outer diameter that coincides with an outer diameter of a nugget portion of the spot welded portion, such that one of the concentric ring-like elements positioned immediately outside the ring-like element closest to the central portion substantially coincides with a circumferential portion of the nugget portion.

6. The evaluation method for a spot welded portion as claimed in claim 5, wherein the elements are formed as rectangular elements except that which is positioned in the proximity of the spot welded portion.

7. The evaluation method for a spot welded portion as claimed in claim 5, wherein the division into the plural concentric ring-like elements is performed such that a ring is divided in a radial direction from a center into three or four layers from a first layer of an innermost layer corresponding to the spot welded portion to a third or fourth layer of an outermost layer.

8. The evaluation method for a spot welded portion as claimed in claim 5, wherein each of the plural concentric ring-like elements is divided into 4 to 8 portions in the circumferential direction.

* * * * *